(12) United States Patent
Mustata et al.

(10) Patent No.: US 9,458,089 B2
(45) Date of Patent: Oct. 4, 2016

(54) PHENOXY ALKYL DIETHANOLAMINE AND DIISOPROPANOLAMINE COMPOUNDS FOR DELIVERING ACTIVE AGENTS

(71) Applicant: EMISPHERE TECHNOLOGIES, INC., Roseland, NJ (US)

(72) Inventors: Gabriela Mustata, Roseland, NJ (US); Dahua Pan, Roseland, NJ (US); David Gschneidner, Roseland, NJ (US)

(73) Assignee: Emisphere Technologies, Inc., Roseland, NJ (US)

( * ) Notice: Subject to any disclaimer, the term of this patent is extended or adjusted under 35 U.S.C. 154(b) by 0 days.

(21) Appl. No.: 14/423,319

(22) PCT Filed: Aug. 22, 2013

(86) PCT No.: PCT/US2013/056221
§ 371 (c)(1),
(2) Date: Feb. 23, 2015

(87) PCT Pub. No.: WO2014/031874
PCT Pub. Date: Feb. 27, 2014

(65) Prior Publication Data
US 2015/0321993 A1    Nov. 12, 2015

Related U.S. Application Data

(60) Provisional application No. 61/692,554, filed on Aug. 23, 2012.

(51) Int. Cl.
C07C 217/62 (2006.01)
A61K 9/00 (2006.01)
A61K 31/575 (2006.01)
A61K 47/18 (2006.01)
C07C 217/20 (2006.01)
A61K 9/20 (2006.01)

(52) U.S. Cl.
CPC .......... *C07C 217/62* (2013.01); *A61K 9/0053* (2013.01); *A61K 31/575* (2013.01); *A61K 47/18* (2013.01); *C07C 217/20* (2013.01); *A61K 9/2004* (2013.01)

(58) Field of Classification Search
CPC    C07C 217/62; C07C 217/20; A61K 9/0053; A61K 47/18; A61K 31/575; A61K 9/2004
See application file for complete search history.

(56) References Cited

U.S. PATENT DOCUMENTS

| 7,297,794 B2 * | 11/2007 | Gschneidner | ........ A61K 9/0095 544/174 |
| 8,148,578 B2 * | 4/2012 | Gschneidner | ........ A61K 31/137 564/305 |
| 2007/0105953 A1 | 5/2007 | Julian | |
| 2009/0253702 A1 | 10/2009 | Castelli | |

FOREIGN PATENT DOCUMENTS

| WO | WO-03/045306 A2 | 6/2003 |
| WO | WO-2005/115406 A2 | 12/2005 |
| WO | WO-2006/072070 A2 | 7/2006 |
| WO | WO-2007/121318 A2 | 10/2007 |
| WO | WO-2011/156563 A2 | 12/2011 |

OTHER PUBLICATIONS

International Search Report issued in PCT/US2013/056221 dated Jan. 15, 2014.

* cited by examiner

*Primary Examiner* — Shailendra Kumar
(74) *Attorney, Agent, or Firm* — Blank Rome LLP

(57) ABSTRACT

The present invention relates to particular phenoxy alkyl diethanolamine and diisopropanolamine compounds for delivering biologically active agents to a target. These compounds are well suited for forming non-covalent mixtures with active agents for oral, intracolonic, pulmonary, and other routes of administration to animals.

21 Claims, No Drawings

PHENOXY ALKYL DIETHANOLAMINE AND DIISOPROPANOLAMINE COMPOUNDS FOR DELIVERING ACTIVE AGENTS

This application is the U.S. national phase of International Application No. PCT/US2013/056221, filed Aug. 22, 2013, which claims the benefit of U.S. Provisional Application No. 61/692,554, filed Aug. 23, 2012, which is hereby incorporated by reference.

FIELD OF THE INVENTION

The present invention relates to particular phenoxy alkyl diethanolamine and diisopropanolamine compounds for delivering biologically active agents to a target. These compounds are well suited for forming non-covalent mixtures with active agents for oral, intracolonic, pulmonary, and other routes of administration to animals.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Certain modified amino acids have been used to deliver pharmaceuticals. See, for example, U.S. Pat. Nos. 5,629,020; 5,643,957; 5,766,633; 5,776,888; and 5,866,536. International Patent Publication Nos. WO 01/32130 and WO 01/32596 disclose particular phenyl amine carboxylic acid compounds and phenoxy carboxylic acid compounds for delivering active agents. International Publication No. WO 00/50386 also discloses amine delivery agents. U.S. Pat. No. 7,297,794 discloses a number of phenoxy amine compounds and compositions for the delivery of active agents.

However, there is still a need for simple, inexpensive, and safe delivery systems which are easily prepared and which can deliver a broad range of active agents by various routes.

SUMMARY OF THE INVENTION

The present inventors have discovered amine-containing delivery agent compounds with reduced hERG activity. hERG inhibition is associated with QT prolongation, an undesired effect. Delivery agent compounds of the present invention include those shown below and salts thereof (including pharmaceutically acceptable salts thereof):

Compound 1

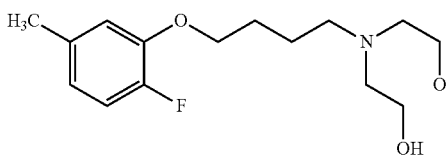

(4-(2-fluoro-5-methylphenoxy)butyldiethanolamine or 2-FPBD)

Compound 2

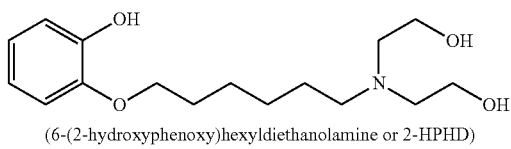

(6-(2-hydroxyphenoxy)hexyldiethanolamine or 2-HPHD)

Compound 3

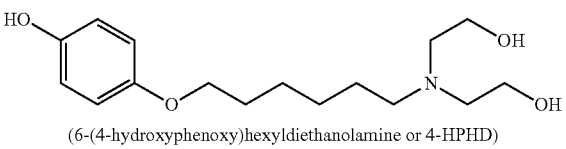

(6-(4-hydroxyphenoxy)hexyldiethanolamine or 4-HPHD)

Compound 4

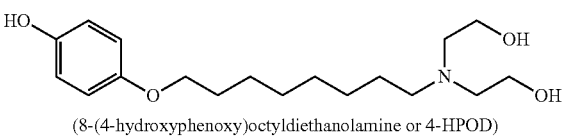

(8-(4-hydroxyphenoxy)octyldiethanolamine or 4-HPOD)

Compound 5

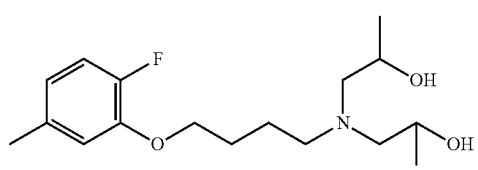

(4-(2-fluoro-5-methylphenoxy)butyldiisopropanolamine or 2-FPBDIP)

Compound 6

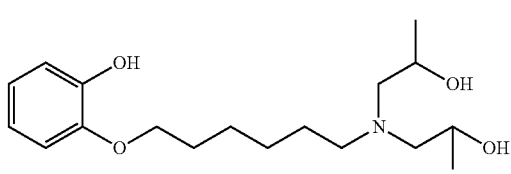

(6-(2-hydroxyphenoxy)hexyldiisopropanolamine or 2-HPHDIP)

Compound 7

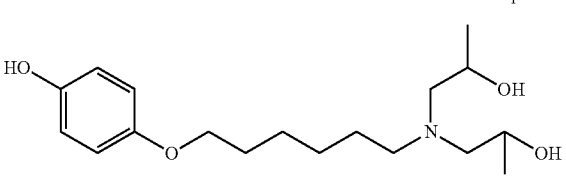

(6-(4-hydroxyphenoxy)hexyldiisopropanolamine or 4-HPHDIP)

Compound 8

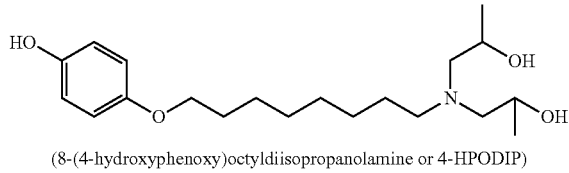

(8-(4-hydroxyphenoxy)octyldiisopropanolamine or 4-HPODIP)

According to one embodiment, the compound is 4-(2-fluoro-5-methylphenoxy)-butyldiethanolamine or a pharmaceutically acceptable salt thereof.

According to another embodiment, the compound is 6-(2-hydroxyphenoxy)-hexyldiethanolamine or a pharmaceutically acceptable salt thereof.

According to another embodiment, the compound is 6-(4-hydroxyphenoxy)-hexyldiethanolamine or a pharmaceutically acceptable salt thereof.

According to another embodiment, the compound is 8-(4-hydroxyphenoxy)-octyldiethanolamine or a pharmaceutically acceptable salt thereof.

According to one embodiment, the compound is 4-(2-fluoro-5-methylphenoxy)-butyldiisopropanolamine or a pharmaceutically acceptable salt thereof.

According to another embodiment, the compound is 6-(2-hydroxyphenoxy)-hexyldiisopropanolamine or a pharmaceutically acceptable salt thereof.

According to another embodiment, the compound is 6-(4-hydroxyphenoxy)-hexyldiisopropanolamine or a pharmaceutically acceptable salt thereof.

According to another embodiment, the compound is 8-(4-hydroxyphenoxy)-octyldiisopropanolamine or a pharmaceutically acceptable salt thereof.

The present invention also provides a pharmaceutical composition comprising a biologically active agent and at least one compound selected from 4-(2-fluoro-5-methylphenoxy)butyldiethanolamine, 6-(2-hydroxyphenoxyl)hexyldiethanolamine, 6-(4-hydroxy-phenoxy)hexyldiethanolamine, 8-(4-hydroxyphenoxyl)octyldiethanolamine, 4-(2-fluoro-5-methylphenoxy)butylddiisopropanolamine, 6-(2-hydroxyphenoxyl)hexyldiisopropanolamine, 6-(4-hydroxy-phenoxy)hexyldiisopropanolamine, 8-(4-hydroxyphenoxyl)octyldiisopropanolamine and pharmaceutically acceptable salts thereof.

In one embodiment, the biologically active agent comprises at least one protein, polypeptide, peptide, hormone, polysaccharide, mucopolysaccharide, carbohydrate, or lipid, and any combination thereof.

In another embodiment, the biologically active agent is selected from: triptans, BIBN-4096BS, growth hormones, human growth hormones recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim. postaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

In yet another embodiment, the biologically active agent comprises insulin, BIBN-4096BS, calcitonin, parathyroid hormone, erythropoietin, growth hormones and any combination thereof.

In yet another embodiment, the biologically active agent comprises insulin.

In yet another embodiment, the biologically active agent is a bisphosphonate. For instance, the bisphosphonate may be selected from alendronate, tiludronate, etidronate, clodronate, pamidronate, olpadronate, incadronate, and mixtures thereof.

In yet another embodiment, the biologically active agent is a triptan, such as sumatriptan, rizatriptan, naratriptan, zolmitriptan, eletriptan, almotriptan, frovatriptan, and avitriptan.

In yet another embodiment, the biologically active agent is erythropoietin.

In yet another embodiment, the active agent is follicle stimulating hormone.

The present invention also provides a dosage unit form (such as a solid dosage form) comprising (a) at least one compound selected from 4-(2-fluoro-5-methylphenoxy)butyldiethanol-amine, 6-(2-hydroxyphenoxyl)hexyldiethanolamine, 6-(4-hydroxyphenoxyl)hexyldiethanolamine, 8-(4-hydroxyphenoxyl)octyldiethanolamine, 4-(2-fluoro-5-methylphenoxy)butylddiisopropanolamine, 6-(2-hydroxyphenoxyl)hexyldiisopropanolamine, 6-(4-hydroxy-phenoxy)hexyldiisopropanolamine, 8-(4-hydroxyphenoxyl)octyldiisopropanolamine, and pharmaceutically acceptable salts thereof and (b) at least one of an excipient, a diluent, a disintegrant, a lubricant, a plasticizer, a colorant, a dosing vehicle, or any combination thereof. The dosage unit form can be, for example, a tablet, capsule, powder, or liquid. The dosing vehicle can be a liquid, such as water, 1,2-propane diol, ethanol, or any combination thereof.

The present invention also provides a method for administering a biologically active agent to an animal (such as a mammal, particularly a human) in need of the agent by administering to the animal a pharmaceutical composition of the present invention. In one preferred embodiment, the pharmaceutical composition is administered orally.

The present invention also provides a method for preparing a composition comprising (a) at least one biologically active agent, (b) at least one compound selected from 4-(2-fluoro-5-methylphenoxy)butyldiethanolamine, 6-(2-hydroxyphenoxyl)hexyldiethanolamine, 6-(4-hydroxy-phenoxy)hexyldiethanolamine, 8-(4-hydroxyphenoxyl)octyldiethanolamine, 4-(2-fluoro-5-methylphenoxy)butylddiisopropanolamine, 6-(2-hydroxyphenoxyl)hexyldiisopropanolamine, 6-(4-hydroxy-phenoxy)hexyldiisopropanolamine, 8-(4-hydroxyphenoxyl)octyldiisopropanolamine and pharmaceutically acceptable salts thereof, and (c) optionally, a dosing vehicle.

DETAILED DESCRIPTION OF THE INVENTION

Delivery Agent Compounds

The delivery agent compounds may be in the form of the free base or salts thereof. Suitable salts include, but are not limited to, organic and inorganic salts, for example ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. In one embodiment, the delivery agent is a salts citrate or mesylate salt.

Salts of the delivery agent compounds of the present invention may be prepared by methods known in the art. For example, citrate salts and mesylate salts may be prepared in ethanol, toluene and citric acid.

The delivery agent compounds may be prepared by alkylation of the corresponding phenol starting material with a 3-fold excess of an unbranched alkyl dibromide of the appropriate length. The resulting mono-alkyl bromide phenoxy ether is reacted with excess diethanol amine to form the free amine compounds which are then treated with an appropriate acid to form the amine salt.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, methyl t-butyl ether, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Suitable polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer may ranges from about 100 to about 200,000 daltons. In one embodiment, the molecular weight of the polymer ranges from about 200 to about 10,000 daltons. In another embodiment, the molecular weight of the polymer ranges from about 200 to about 600 daltons or from about 300 to about 550 daltons.

Biologically Active Agents

Biologically active agents suitable for use in the present invention include pharmacological agents and therapeutic agents. Suitable active agents include those that are rendered less effective, ineffective or are destroyed in the gastro-intestinal tract by acid hydrolysis, enzymes and the like.

Also included as suitable active agents are those macromolecular agents whose physiochemical characteristics, such as, size, structure or charge, prohibit or impede absorption when dosed orally.

For example, biologically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α (e.g., interferon alfacon-1 (available as Infergen® from InterMune, Inc. of Brisbane, Calif.)), β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; glucagon-like peptide 1 (GLP-1); anti-microbials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof. Non-limiting examples of triptans include sumatriptan, rizatriptan, naratriptan, zolmitriptan, eletriptan, almotriptan, frovatriptan, and avitriptan.

Delivery Systems

The composition of the present invention comprises one or more delivery agent compounds of the present invention, and one or more biologically active agents. In one embodiment, one or more of the delivery agent compounds, or salts of these compounds, may be used as a delivery agent by mixing it with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternatively, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects. In one embodiment, the molar ratio of the delivery agent to the active agent ranges from about 0.5:1 to about 500:1. In one embodiment, the molar ratio of the delivery agent to the active agent is about 250:1.

The presently disclosed delivery agent compounds facilitate the delivery of biologically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically active agents to any animals, including but not limited to birds such as chickens; mammals, such as rodents, cows, pigs, dogs, cats, primates, and particularly humans; and insects.

The system is particularly advantageous for delivering chemically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions of the present invention provide increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment, suppression, or prevention of a disease or for achieving a desired physiological effect, such as those listed in the table below, in an animal by administering the composition of the present invention. Preferably, an effective amount of the composition for the treatment, suppression, or prevention of the desired disease or for achieving the desired physiological effect is administered. Specific indications for active agents can be found in the Physicians' Desk Reference ($64^{th}$ Ed., 2009, PDR Network, LLC), which is herein incorporated by reference. The active agents in the table below include their analogs, fragments, mimetics, and polyethylene glycol-modified derivatives.

| Active Agent | Disease and Physiological Effect |
| --- | --- |
| Growth hormones (including human recombinant growth hormone and growth-hormone releasing factors and its analogs) | Growth disorders |
| Interferons, including $\alpha$, $\beta$ and $\gamma$. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |

| Active Agent | Disease and Physiological Effect |
|---|---|
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |
| BIBN4096BS – (1-Piperidinecarboxamide. N-[2-[ [ 5-amino-1-[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*, S*)]-) | Anti-migraine; calcitonin gene-related peptide antagonist |
| Triptans (e.g., sumatriptan, rizatriptan, naratriptan, zolmitriptan, eletriptan, almotriptan, frovatriptan, and avitriptan) | Migraines; Anti-migraine effect; pain |

For example, one embodiment of the present invention is a method for treating a patient suffering from or susceptible to diabetes by administering insulin and at least one of the delivery agent compound of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

EXAMPLES

The following examples illustrate the invention without limitation. All parts are given by weight unless otherwise indicated.

Proton nuclear magnetic resonance ($^1$H NMR) analyses for the compounds listed below were conducted on a 400 MHz JEOL spectrometer using dimethyl sulfoxide (DMSO-$d_6$) as the solvent unless otherwise indicated.

Example 1

Preparation of Compounds

1. Preparation of Compound 1

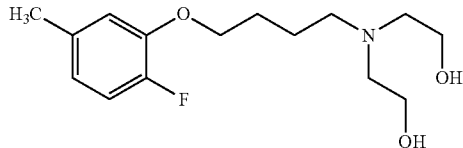 [SMILES: Cc1ccc(F)c(OCCCCN(CCO)CCO)c1]

4-(2-fluoro-5-methylphenoxy)butyldiethanolamine: A solution of 150 g (1.19 moles) 2-fluoro-5-methylphenol, 770.4 g (3.57 moles) of 1,4-dibromobutane and 600 mL of ethanol was treated with 180.6 g (1.31 moles) of potassium carbonate and heated to reflux for 3 hours. After cooling to 25° C., the solids were removed by filtration. The solvent from the filtrate was stripped off and re-filtered. This filtrate was vacuum distilled to remove the excess dibromobutane. The product was used as is from the distillation pot.

The crude 4-(2-fluoro-5-methylphenoxy)butyl bromide (295.0 g) was mixed with 1 kg of diethanolamine and heated slowly to 70° C. After 3 hours at 70° C., the reaction mixture was cooled to 25° C. and treated with 1.0 L of 1N sodium hydroxide. This mixture was washed with ethyl acetate (3×330 mL). The combined organic phases were washed with water.

After drying over sodium sulfate the organic layer was treated with gaseous hydrogen chloride. The solvents were stripped off and the product crystallized from ethanol and methyl t-butyl ether. The solid was dried in a vacuum oven to yield the hydrochloride salt of 4-(2-fluoro-5-methylphenoxy)butyldiethanolamine. Melting point: 83-86° C. $^1$H NMR Analysis: (d$^6$-DMSO): δ 9.77, bs, 1H (R$_3$N$^+$H); δ 7.01, d, 1H (arylH); δ 6.95, d, 1H (arylH); δ 6.69, dd, H (arylH); δ 5.30, bs, 2H (OH); δ 4.01, t, 2H, (CH$_2$ α to ArO); δ 3.74, t, 4H, (CH$_2$'s α to OH); δ 3.20, m, 6H, (CH$_2$'s α to N); δ 2.23, s, 3H, CH$_3$); δ 1.84, m, 2H (CH$_2$ in chain); δ 1.73, m, 2H (CH$_2$ in chain). $^{13}$C NMR (d6-DMSO): 151.2, 148.71, 145.86, 134.06, 121.06, 115.51, 67.95, 55.23, 54.75, 52.86, 25.82, 20.63, 19.93.

2. Preparation of Compound 2

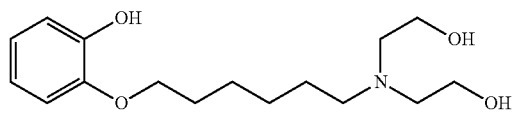 [SMILES: OCCN(CCO)CCCCCCOc1ccccc1O]

6-(2-hydroxyphenoxyl)hexyldiethanolamine: A solution of 200 g (1.00 moles) 2-benzyloxyphenol, 731 g (3.00 moles) of 1,6-dibromohexane and 700 mL of ethanol was treated with 152 g (1.10 moles) of potassium carbonate and heated to reflux for 3 hours. After cooling to 25° C., the solids were removed by filtration. The solvent from the filtrate was stripped off and re-filtered. This filtrate was vacuum distilled to remove the excess dibromohexane. The product was used as is from the distillation pot.

The crude 6-(2-benzyloxyphenoxyl)hexyl bromide (350 g) was mixed with 1 kg of diethanolamine and heated slowly to 70° C. After 3 hours at 70° C., the reaction mixture was cooled to 25° C. and treated with 1.0 L of 1N sodium hydroxide. This mixture was washed with ethyl acetate (3×330 mL). The combined organic phases were washed with water. After drying over sodium sulfate the organic layer was concentrated and used as is.

Crude 6-(2-benzyloxyphenoxyl)hexyldiethanolamine (150 g, 0.387 moles) was charged in a 500 ml Parr shaker jar along with 150 ml of ethanol. This mixture was treated with 0.65 g of 10% palladium on carbon and placed under an atmosphere of hydrogen gas at 50-55 psi. After 1 equivalent of hydrogen gas has been taken up (typically 20 hours), the catalyst was removed by filtration, and the filtrate was quickly treated with gaseous hydrogen chloride. Methyl t-butyl ether was added producing a free stirring slurry. The solid was isolated by filtration and dried in a vacuum oven to yield the hydrochloride salt of 6-(2-hydroxyphenoxyl) hexyldiethanolamine. Melting point: 95-97° C. $^1$H NMR Analysis: ($d^6$-DMSO): δ 9.63, bs, 1H ($R_3N^+H$); δ 8.75, s, 1H (arylOH); 6.82, dd, 1H (arylH); δ 6.75, td, 1H (arylH); δ 6.62, m, 2H (arylH); δ 5.24, bs, 2H (OH); δ 3.87, t, 2H, ($CH_2$ α to ArO); δ 3.70, t, 4H, ($CH_2$'s α to OH); δ 3.16, m, 4H, ($CH_2$'s α to N); δ 3.12, m, 2H, ($CH_2$ α to N); δ 1.64, m, 4H ($CH_2$ in chain); δ 1.40, p, 2H ($CH_2$ in chain); δ 1.29, p, 2H ($CH_2$ in chain). $^{13}$C NMR (d6-DMSO): 146.85, 146.85, 120.90, 119.10, 115.65, 113.73, 68.05, 55.28, 54.66, 53.11, 28.54, 25.8, 25.00, 22.7.

3: Preparation of Compounds 3 and 4

Compounds 3 and 4 were synthesized by the same method as Compound 2 starting with 4-benzyloxyphenol and the appropriate dialkyl bromide (hexyl or octyl, respectively).

Characterization of Compound 3, the hydrochloride salt of 6-(4-hydroxyphenoxyl)hexyldiethanolamine. $^1$H NMR Analysis: (d6-DMSO): δ 9.75, bs, 1H ($R_3N^+H$); δ 8.92, s, 1H (arylOH); 6.70, d, 2H (arylH); δ 6.65, d, 2H (arylH); δ 5.29, bs, 2H (OH); δ 3.82, t, 2H, ($CH_2$ α to ArO); δ 3.75, t, 4H, ($CH_2$'s α to OH); δ 3.20, m, 4H, ($CH_2$'s α to N); δ 3.12, m, 2H, ($CH_2$α to N); δ 1.66, m, 4H ($CH_2$ in chain); δ 1.38, p, 2H ($CH_2$ in chain); δ 1.31, p, 2H ($CH_2$ in chain). $^{13}$C NMR (d6-DMSO): 151.39, 151.13, 115.67, 115.28, 67.65, 55.31, 54.70, 53.12, 28.57, 25.8, 25.07, 22.7.

Characterization of Compound 4, the hydrochloride salt of 8-(4-hydroxyphenoxy)octyldiethanolamine. $^1$H NMR Analysis: (d6-DMSO): δ 9.69, bs, 1H ($R_3N^+H$); δ 8.89, s, 1H (arylOH); 6.69, d, 2H (arylH); δ 6.64, d, 2H (arylH); δ 5.30, bs, 2H (OH); δ 3.81, t, 2H, ($CH_2$ α to ArO); δ 3.74, t, 4H, ($CH_2$'s α to OH); δ 3.20, m, 4H, ($CH_2$'s α to N); δ 3.12, m, 2H, ($CH_2$ α to N); δ 1.63, m, 4H ($CH_2$ in chain); δ 1.35, m, 8H ($CH_2$ in chain). $^{13}$C NMR (d6-DMSO): 151.41, 151.08, 115.66, 115.28, 67.79, 55.28, 54.67, 53.16, 28.78, 28.44, 25.8, 25.1, 22.6.

Compounds 5-8 may be made using the same methods as Compounds 1-4, substituting diisopropanolamine for diethanolamine, as appropriate.

Example 2 hERG Affinity Experiments

A series of computational models were built using compounds with known experimental hERG values. A consensus model that combines the results from three different models was used to predict an individual compound's hERG activity. The $IC_{50}$ thresholds used for classifying compounds is given below:

"****"—<2.0 µM (High)
"***"—2.0-5.0 µM (Medium)
"**"—5.0-50.0 µM (Low)
"*"—>50.0 µM (Very Low)

| Compound | Predicted hERG Activity |
|---|---|
| 2-FPBD | ** |
| 2-HPHD | ** |
| 4-HPHD | * |
| 4-HPOD | * |

Below is a table of the predicted and observed hERG activities of various compounds.

| Compound | Predicted hERG Activity | Experimental hERG Activity |
|---|---|---|
| 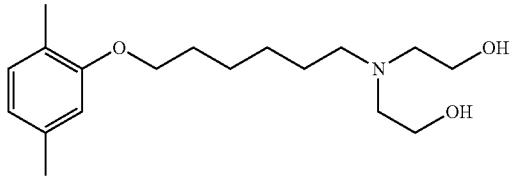 [SMILES: Cc1ccc(C)c(OCCCCCCN(CCO)CCO)c1] | ** | ** |
| 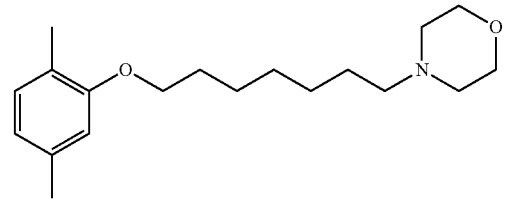 [SMILES: Cc1ccc(C)c(OCCCCCCCN2CCOCC2)c1] | ** | ** |
| 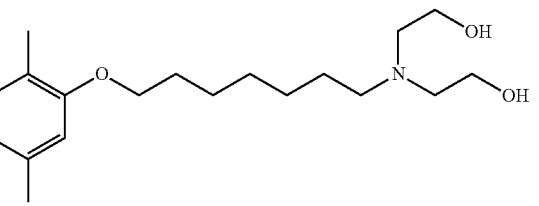 | ** | ** |

-continued

| Compound | Predicted hERG Activity | Experimental hERG Activity |
|---|---|---|
| (structure) | **** | Not determined |
| (structure) | * | * | hERG activity was measured using a patch clamp method on clone hERG channels in mammalian cells. The concentration of test articles was 1 μm and a comparison was made to both a positive (cisapride) and negative (vehicle) control.

Example 3

Delivery of Trodusquemine

The oral delivery of trodusquemine in rats (250-300 g rats) using the delivery agent compounds of the present invention was evaluated as follows. Mini-tablets containing 3.8 mg of trodusquemine and 30 mg of delivery agent were prepared. Each rat was administered two mini-tablets to provide a total dose of 25 mg/kg of trodusquemine and 200 mg/kg delivery agent. Blood samples were collected serially by retro-orbital bleeding and were taken before administration and at 1, 3, 6, 10, 24 hours after administration. The plasma was assayed for the amount of trodusquemine present.

The results (with the standard deviations included) are shown in the table below.

| Delivery Agent | $C_{max}$ (ng/mL) | $AUC_{last}$ (ng*hr/ml) | $T_{max}$ (hours) |
|---|---|---|---|
| None | 274 ± 71.2 | 2419 ± 2487 | 7.6 ± 2.2 |
| 2-FPBD | 1508 ± 1715 | 20839 ± 22436 | 3.4 ± 2.5 |
| 2-HPHD | 853 ± 954 | 13747 ± 12781 | 3.3 ± 2.1 |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound selected from

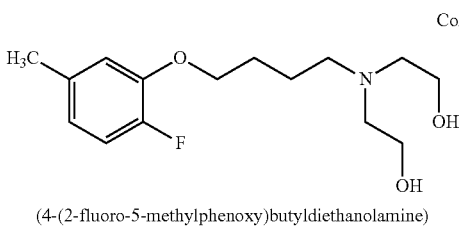

Compound 1

(4-(2-fluoro-5-methylphenoxy)butyldiethanolamine)

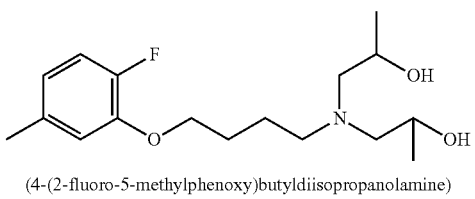

Compound 5

(4-(2-fluoro-5-methylphenoxy)butyldiisopropanolamine)

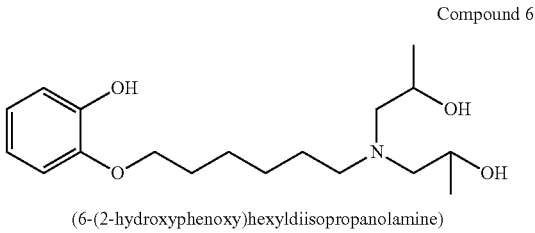

Compound 6

(6-(2-hydroxyphenoxy)hexyldiisopropanolamine)

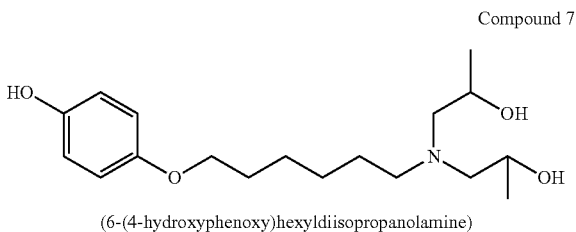

Compound 7

(6-(4-hydroxyphenoxy)hexyldiisopropanolamine)

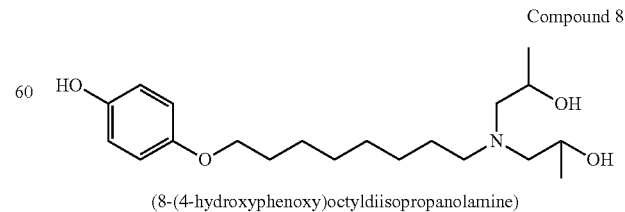

Compound 8

(8-(4-hydroxyphenoxy)octyldiisopropanolamine)

and salts thereof.

2. The compound of claim 1, wherein the compound is

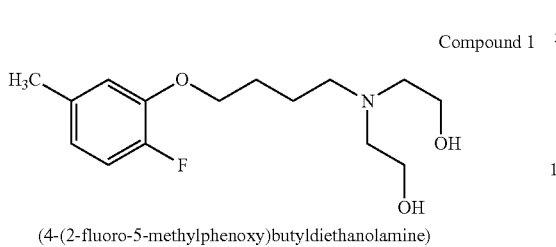

(4-(2-fluoro-5-methylphenoxy)butyldiethanolamine)

or a salt thereof.

3. The compound of claim 1, wherein the compound is

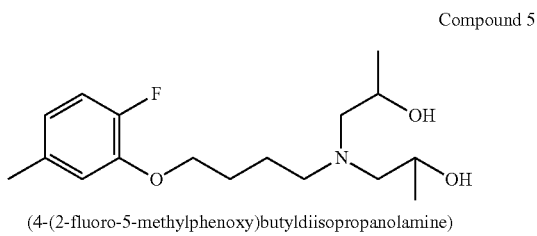 [SMILES: Cc1ccc(F)c(OCCCCN(CC(C)O)CC(C)O)c1]

(4-(2-fluoro-5-methylphenoxy)butyldiisopropanolamine)

or a salt thereof.

4. The compound of claim 1, wherein the compound is

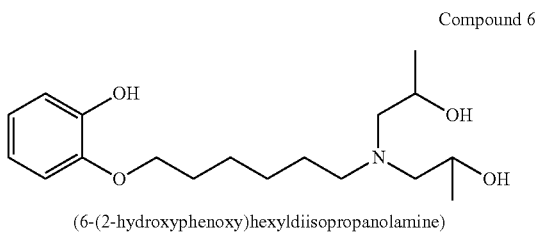 [SMILES: CC(O)CN(CCCCCCOc1ccccc1O)CC(C)O]

(6-(2-hydroxyphenoxy)hexyldiisopropanolamine)

or a salt thereof.

5. The compound of claim 1, wherein the compound is

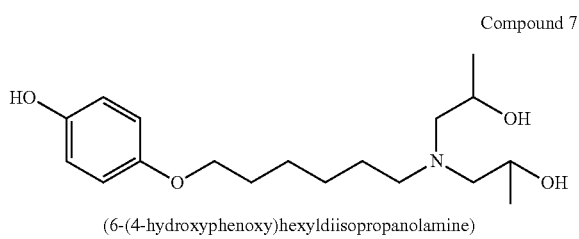 [SMILES: CC(O)CN(CCCCCCOc1ccc(O)cc1)CC(C)O]

(6-(4-hydroxyphenoxy)hexyldiisopropanolamine)

or a salt thereof.

6. The compound of claim 1, wherein the compound is

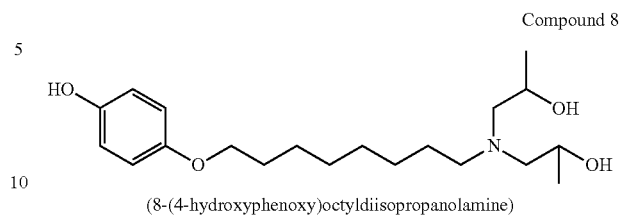

(8-(4-hydroxyphenoxy)octyldiisopropanolamine)

or a salt thereof.

7. A pharmaceutical composition comprising:
(A) a biologically active agent; and
(B) a compound of claim 1.

8. The pharmaceutical composition of claim 7, wherein the biologically active agent comprises at least one protein, polypeptide, peptide, hormone, polysaccharide, mucopolysaccharide, carbohydrate, or lipid, and any combination thereof.

9. The pharmaceutical composition of claim 7, wherein the biologically active agent is selected from the group consisting of: triptans, BIBN-4096BS, growth hormones, human growth hormones recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (TGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

10. The pharmaceutical composition of claim 7, wherein the biologically active agent comprises a triptan, insulin, BIBN-4096BS, calcitonin, parathyroid hormone, erythropoietin, growth hormones and any combination thereof.

11. A dosage unit form comprising:
(A) a pharmaceutical composition of claim 7; and
(B) at least one of
    (a) an excipient,
    (b) a diluent,
    (c) a disintegrant,
    (d) a lubricant,
    (e) a plasticizer,
    (f) a colorant,
    (g) a dosing vehicle, or
    (h) any combination thereof.

12. A method for administering a biologically active agent to an animal in need of the agent, the method comprising administering orally to the animal a pharmaceutical composition of claim 7.

13. A method for preparing a composition comprising mixing:
(A) at least one biologically active agent;
(B) at least one compound of claim 1; and
(C) optionally, a dosing vehicle.

14. A compound selected from

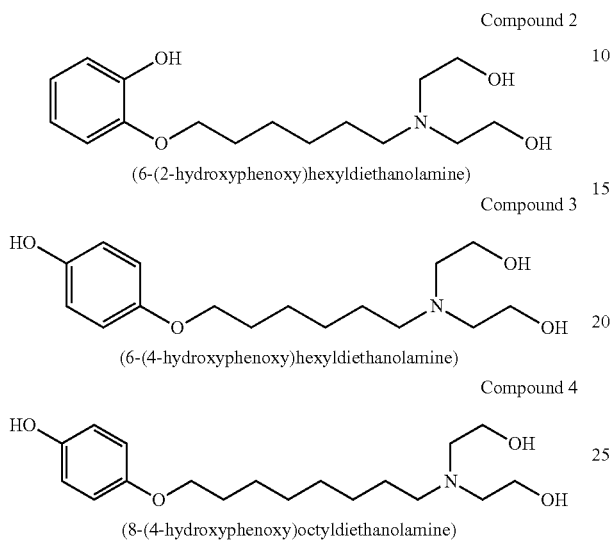

and pharmaceutically acceptable salts thereof.

15. The pharmaceutical composition of claim 7, wherein the biologically active agent is selected from the group consisting of: BIBN-4096BS, growth hormones, human growth hormones recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

16. The pharmaceutical composition of claim 7, wherein the biologically active agent comprises insulin, BIBN-4096BS, calcitonin, parathyroid hormone, erythropoietin, growth hormones and any combination thereof.

17. A pharmaceutical composition comprising:
(A) a biologically active agent; and
(B) a compound of claim 14;
wherein the biologically active agent is selected the group consisting of: BIBN-4096BS, growth hormones, human growth hormones recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

18. The pharmaceutical composition of claim 17, wherein the biologically active agent is selected from the group consisting of insulin, BIBN-4096BS, calcitonin, parathyroid hormone, erythropoietin, growth hormones and any combination thereof.

19. The compound of claim 14, wherein the compound is

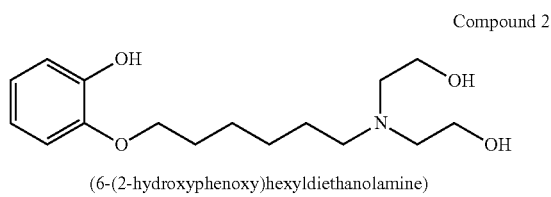 [SMILES: OCCN(CCO)CCCCCCOc1ccccc1O]

or a pharmaceutically acceptable salt thereof.

20. A pharmaceutical composition comprising:
(A) a biologically active agent; and
(B) the compound of claim 19.

21. A method for administering a biologically active agent to an animal in need of the agent, the method comprising administering orally to the animal a pharmaceutical composition of claim 20.

* * * * *